US007293426B2

(12) United States Patent
Heuser

(10) Patent No.: US 7,293,426 B2
(45) Date of Patent: Nov. 13, 2007

(54) APPARATUS FOR FREEZING A BIOLOGICAL SAMPLE

(75) Inventor: John E. Heuser, Clayton, MO (US)

(73) Assignee: Washington University, St. Louis, MO (US)

( * ) Notice: Subject to any disclaimer, the term of this patent is extended or adjusted under 35 U.S.C. 154(b) by 238 days.

(21) Appl. No.: 10/962,810

(22) Filed: Oct. 5, 2004

(65) Prior Publication Data

US 2006/0070392 A1  Apr. 6, 2006

(51) Int. Cl.
*F25D 17/02*  (2006.01)
*F25C 1/00*  (2006.01)

(52) U.S. Cl. ............................................. 62/373; 62/66

(58) Field of Classification Search .................. 62/373, 62/371, 457.9, 614; 29/407.01, 407.05, 407.08, 29/559
See application file for complete search history.

(56) References Cited

U.S. PATENT DOCUMENTS

| | | | |
|---|---|---|---|
| 4,408,469 A | | 10/1983 | Forth |
| 4,563,883 A | * | 1/1986 | Sitte ........................... 62/51.1 |
| 4,567,847 A | | 2/1986 | Linner |
| 4,676,070 A | | 6/1987 | Linner |
| 4,688,387 A | | 8/1987 | Conaway |
| 4,745,764 A | | 5/1988 | Sitte et al. |
| 4,751,828 A | * | 6/1988 | Coulter et al. ............... 62/51.1 |
| 4,807,442 A | | 2/1989 | Linner et al. |
| 4,827,736 A | | 5/1989 | Miura et al. |
| 4,865,871 A | | 9/1989 | Livesey et al. |
| 4,964,280 A | | 10/1990 | Piunno et al. |
| 4,995,700 A | | 2/1991 | Barney et al. |
| 5,044,165 A | | 9/1991 | Linner et al. |
| D323,895 S | | 2/1992 | Protzmann |
| 5,364,756 A | | 11/1994 | Livesey et al. |
| 6,269,649 B1 | | 8/2001 | Studer |
| 2002/0079318 A1 | | 6/2002 | Wurzinger |

OTHER PUBLICATIONS

MED-VAC Inc., The New Cryopress . . . the definitive quick-freezing device, brochure, 3 pages, date unknown, admitted prior art.
International Search Report from PCT/US05/35880, dated Aug. 4, 2006, 2 pages.

* cited by examiner

*Primary Examiner*—Cheryl Tyler
*Assistant Examiner*—Michael J. Early
(74) *Attorney, Agent, or Firm*—Senniger Powers

(57) ABSTRACT

An apparatus for freezing a biological sample having a frame, an enclosure adapted to conduct a cryogenic fluid therethrough, and a block in the enclosure such that the block is cooled to a temperature capable of freezing the sample. A force generating device is mounted on the frame generally above the enclosure. A sample holder is removably attached to the force generating device having a cavity at its free end for receiving a sample to be frozen. The force generating device, sample holder, and block are constructed to compress the sample between the block and the sample holder such that the holder penetrates the surface of the block and effectively seals the sample during compression.

29 Claims, 4 Drawing Sheets

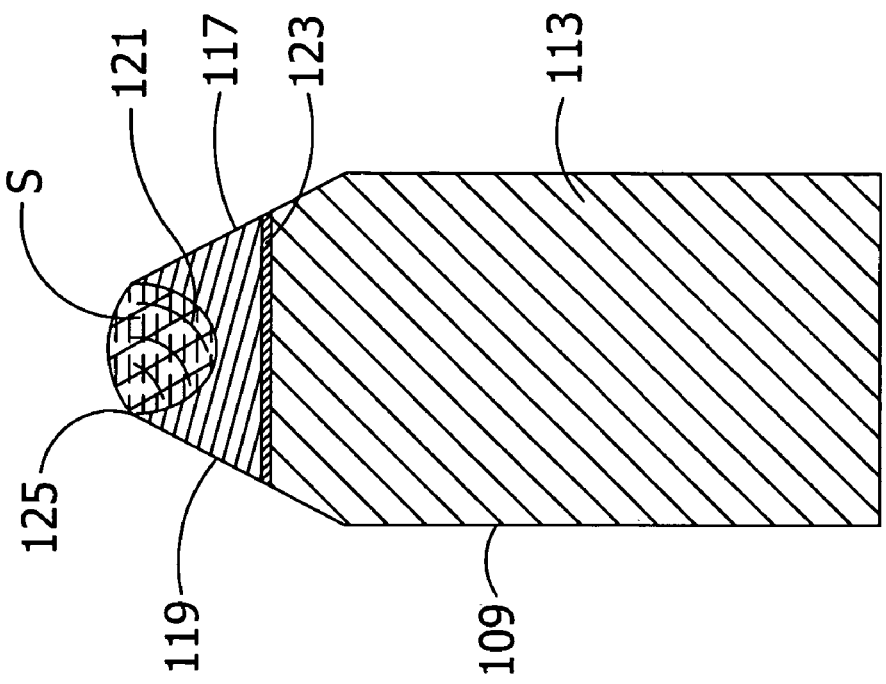
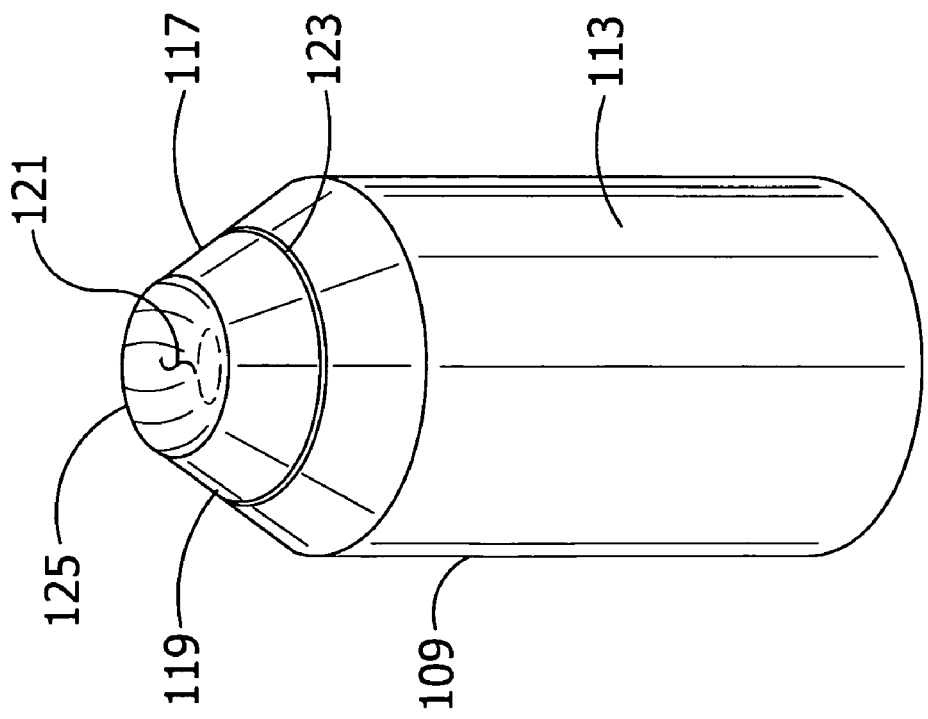

APPARATUS FOR FREEZING A BIOLOGICAL SAMPLE

BACKGROUND OF THE INVENTION

This invention relates generally to a freezing apparatus and more particularly to a high pressure freezing apparatus for preserving biological samples.

It is well-known in the medical arts that to examine biological samples and determine the cellular structure and function thereof, the samples must be "fixed" with minimal alteration of the structural integrity of the cells making up the sample. Typically, freezing machines are used to freeze a biological sample to preserver the structural integrity of the sample. The biological samples to be examined may include samples suspended in an solution as well as human or animal tissue segments and entire organs for transplant or virtually any other material that is desirable for study and examination of cellular structure. The freezing machines create a zone of freezing as thick as possible in the sample so that the cellular structure is preserved in a state that promotes the examination thereof.

When ice crystals form in a living cell or tissue they first extract the water from the cell and form pure ice with nothing dissolved in them (e.g., they form as "snowflakes"). The ice crystal formation not only physically "stabs" the cell to death, but it compresses all its living molecules into narrower and narrower interstices between the growing snowflakes. The compressed molecules are subjected to very abnormal salt and electrolyte compositions and very abnormal packing, resulting in gross distortion of cellular structure, and ultimately, by the end of the freezing process, in cell death. To avoid the gross mechanical deformations that occur to cells and to the molecules within them when their water is converted to crystalline ice, the zone of freezing in a sample to be examined should be accomplished at high pressures (at least 2000 bar) so that water in the sample cannot expand or crystallize as it freezes.

One existing freezing machine, sold under the trade name CRYOPRESS by MedVac Inc. of St. Louis, Mo., uses gravity to "slam" a biological sample onto an ultra-cold block of metal cooled to minus 177 degrees C., the temperature of liquid nitrogen, or to minus 269 degrees C., liquid helium temperature. Another earlier machine designed by others and sold by Lifecell, Inc., of San Antonio, Tex., uses a pneumatic cylinder to slam the sample onto the ultra-cold block. The basic limitation of all such devices is that they properly freeze only a very thin layer (about 5-10 microns) at the surface of the sample that strikes the ultra cold metal block. Also, all such existing "freeze-slammers" incorporate spring-dampers to prevent the sample from bouncing off the cold metal block. Frequently, the dampers do not effectively prevent bounce resulting in non-uniform freezing in the sample.

More importantly, none of these devices are designed to apply pressure to the sample as it strikes the cryo-block. On the contrary, they are designed to absorb pressure so as to prevent bounce (as mentioned above). Current designs of high-pressure freezing machines rely on injecting a cryogenic fluid into a vessel containing the sample, in order to accomplish freezing during the application of high pressure. However, these designs freeze relatively slowly, because a liquid cryogen is applied to the sample rather than a metallic surface that is held at cryogenic temperatures, which is much more conductive of heat. Other shortcomings of existing high-pressure freezing machines include the fact that they are expensive to manufacture and are difficult to operate, and are highly unreliable as a result of the complex mechanical processes that are required to generate and maintain elevated pressures with cryogenic liquids.

Therefore, a need exists for a high-pressure freezing machine that is dependable, inexpensive to manufacture and operate, and that both freezes as fast as possible and sustains as much pressure as possible, in order to produce the best possible freezing.

SUMMARY OF THE INVENTION

Among the several objects of this invention may be noted the provision of an apparatus for freezing material samples that produces a sample having a layer of freezing of increased depth; the provision of such an apparatus that produces a sample having a layer of freezing substantially free of ice crystallization; the provision of such an apparatus that is economical to assemble and operate; the provision of such an apparatus that is reliable; the provision of such an apparatus that produces consistent and easily reproducible results; and the provision of such an apparatus that is capable of handling large samples.

In general an apparatus for freezing a biological sample comprises a frame, an enclosure adapted to conduct a cryogenic fluid therethrough, and a block in the enclosure such that the block is cooled to a temperature capable of freezing the sample. A force generating device is mounted on the frame generally above the enclosure. A sample holder is removably attached to the force generating device having a cavity at its free end for receiving a sample to be frozen. The force generating device, sample holder, and block are constructed to compress the sample between the block and the sample holder such that the holder penetrates the surface of the block and effectively seals the sample during compression.

Another aspect of the invention is directed to a sample holder for use in a freezing apparatus for freezing a sample for microscopic evaluation by using a force generating device to press the sample against a cold block. The sample holder comprises a body adapted to be attached to the force generating device. The body has a cavity at its free end adapted to receive a sample to be frozen. The free end of the body has an edge margin adapted to sealingly engage the block of the freezing apparatus so that the sample held in the cavity is compressed between the block and the body of the sample holder. The edge margin of the holder is adapted to penetrate a surface of the cold block.

In yet another aspect of the invention, a method of freezing a sample for biological evaluation is provided. The method generally comprises lowering the temperature of a metal block to a temperature capable of freezing the sample. A sample is loaded into a sample holder. The sample holder is attached to a force generating device. The force generating device is operated so that the sample is cooled by contact with the block and the sample holder penetrates a surface of the block sealing the cavity and compressing the sample between the sample holder and the block.

Other objects and features of the present invention will be in part apparent and in part pointed out hereinafter.

BRIEF DESCRIPTION OF THE DRAWINGS

FIG. 2 is a perspective of a sample holder of the freezing apparatus;

FIG. 3 cross-section of the sample holder with a sample loaded into a cavity of the holder;

Corresponding parts are designated by corresponding reference numbers throughout the drawings.

DESCRIPTION OF PREFERRED EMBODIMENTS

Figure 1:
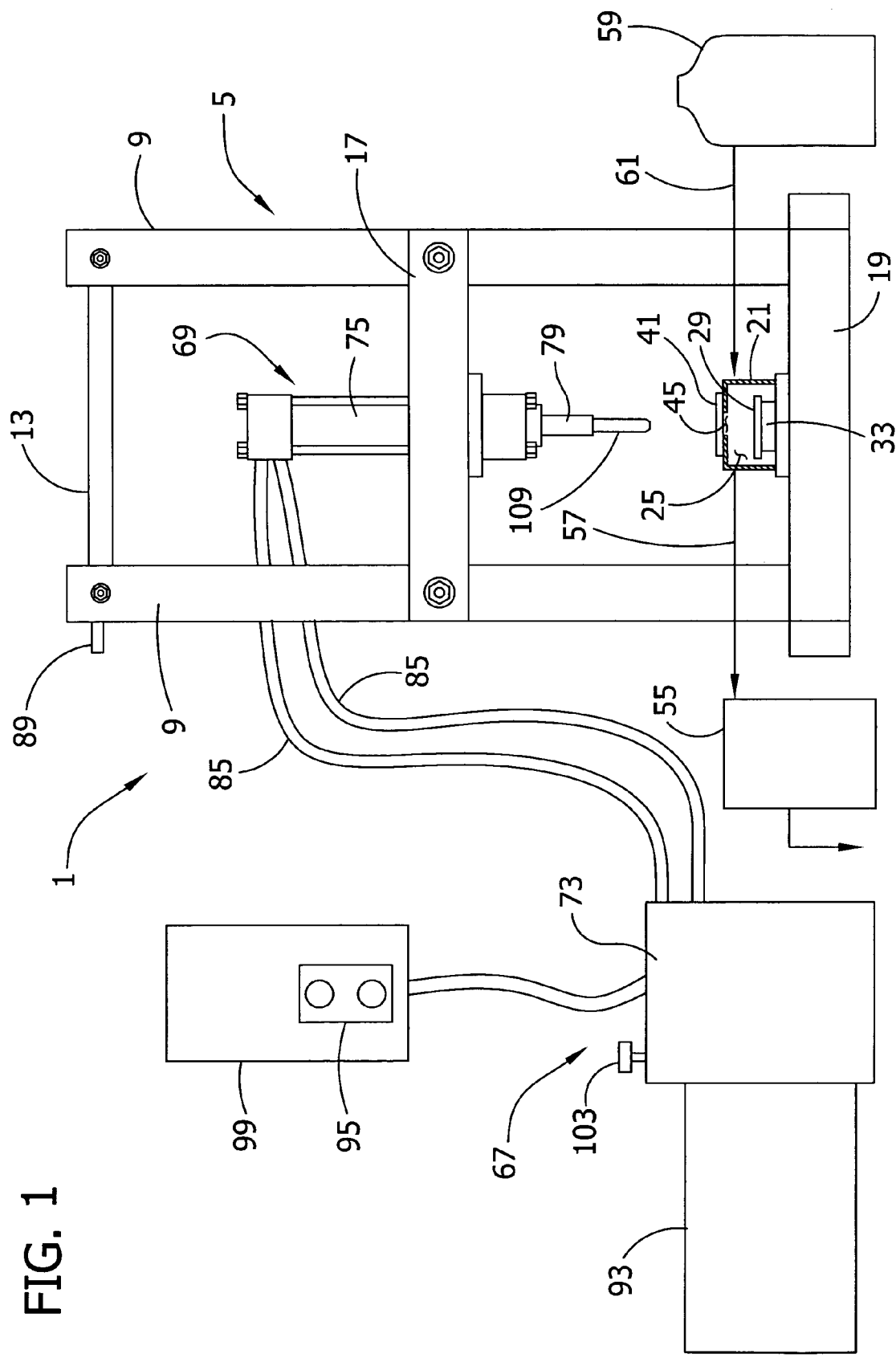
FIG. 1 is a schematic elevation view of freezing apparatus of the present invention.

Referring to FIG. 1, a freezing apparatus of the present invention is designated in its entirety by the reference numeral 1. The freezing apparatus may be commonly referred to as a "slam-freezer", "high-pressure slam-freezer", "freezing machine", or "freezing device". The apparatus 1 is used to freeze a sample of biological material that may comprise human or animal organ tissue samples or any other material to be prepared for microscopic evaluation and study. Typically, the cellular structure of the frozen sample is examined under high magnification by using an electron microscope. It will be understood that the size of the freezing apparatus 1 could be increased to accommodate larger biological samples such as larger tissue samples or entire organs from animals or humans that may be preserved for transplantation.

As shown in FIG. 1, the apparatus 1 comprises a frame generally indicated 5 having two spaced apart upright members 9, a top cross-member 13, two intermediate cross-members 17 (one of which is shown), and a pedestal 19 at the bottom of the frame for supporting the apparatus on a flat surface. The pedestal 19 supports an enclosure 21 that houses a cryogenic chamber 25. The enclosure 21 is shown in section in the drawings to reveal internal construction. A metal block 29 is housed in the cryogenic chamber 25 and is supported therein by a stand 33. The block 29 is in the form of a disk made of a material having high thermal conductivity (e.g., high-purity copper, gold, silver, etc). In the preferred embodiment, the block 29 comprises a 99.99% pure copper disk but it will be understood that the block may comprise other materials and shapes without departing from the scope of this invention. In one embodiment, the stand 33 is a solid piece of stainless steel mounted on the bottom of the enclosure 21 that supports the thermally conductive block 29. To reduce operating costs of the invention, the stand 33 and block 29 in the illustrated embodiment are separate pieces so that only the block must be replaced with each operation of the invention. It will be understood that the stand 33 and block 29 may be combined into a single piece of thermally conductive material (e.g., copper) without departing from the scope of this invention.

The enclosure 21 comprises a moveable lid 41 that covers an opening 45 in a top wall 47 of the enclosure. The moveable lid 41 may be manually positioned or may be connected to an actuator (not shown) such as an air cylinder that may be automatically operated during operation of the freezing apparatus 1. In the illustrated embodiment, the enclosure 21 is connected to a vacuum pump 55 mounted near the frame 5 that evacuates air from the enclosure via piping 57. A cryogenic fluid storage vessel 59 is connected to the enclosure by piping 61. A valve (not shown) in the piping 61 may be used to control the flow of cryogenic fluid from the vessel 59 to the enclosure 21. The cryogenic fluid is typically stored under positive pressure (e.g., about 22 psi or 1.55 kg/cm$^2$) in vessel 59 so that when the valve in the piping 61 is opened cryogenic fluid flows into the enclosure 21. The stand 33 and block 29 are cooled by contact with the cryogenic fluid flowing into the chamber 25. For example, the stand 33 and block 29 may be cooled to a temperature approximately equal to the temperature of the cryogenic fluid (i.e., approximately minus 177 degrees C. for liquid nitrogen or minus 273 degrees C. for liquid helium). Once the cryogenic fluid contacts the stand 33 and/or block 29, heat is transferred from the stand and block to the cryogenic fluid vaporizing the fluid. The negative pressure created by the vacuum pump 55 conveys air out of the enclosure 21 to prevent the block 29 from frosting during cool-down.

The lid 41 is moveable between an open position allowing access to the cryogenic chamber 25 from the top of the enclosure 21 and a closed position covering the opening 45 in the enclosure. The closed position of the lid 41 promotes cooling of the block 29 by isolating the cryogenic chamber 25 from the relatively warm air outside of the chamber as the block is being cooled by the cryogenic fluid. Prior to opening the lid 41, the vacuum in the enclosure 29 is broken by injecting a flow a dry nitrogen gas into the chamber 25. It will be understood that the enclosure 21 may comprise an open ended structure not having a lid (e.g., cup or bucket) that may be manually filled with cryogenic fluid to cool the block 29 and stand 33 to a temperature approximately equal to that of the cryogenic fluid. The block 29 may be cooled by any other method that results in the block being cooled to a temperature substantially below zero degrees Celsius without departing from the scope of this invention.

Referring again to FIG. 1, the freezing apparatus 1 comprises a force generating device, generally indicated 67, in the form of a hydraulic cylinder unit, generally indicated 69, operatively connected to a hydraulic pump 73. The hydraulic cylinder unit 69 is mounted between the two intermediate cross-members 17 generally above the cryogenic chamber 25. In one embodiment, the hydraulic cylinder unit 69 has a cylinder 75 that houses a moveable piston (not shown) attached to a piston rod 79 that extends from the cylinder. The cylinder unit 69 is positioned on the frame 5 so that the piston rod 79 extends downward from the cylinder 75 generally toward the enclosure 21 supported on the pedestal 19 of the frame. A suitable hydraulic cylinder unit 69 is manufactured by Sheffer, Inc. of Cincinnati, Ohio, Model No. 2HHFF6K, having a four inch bore and six inch stroke, a piston rod diameter of approximately 1⅜", and being rated for a maximum sustainable pressure of 3000 psi (207 bar), a maximum shock pressure of 5000 psi (345 bar), and a safety factor of 3.1.

Referring again to FIG. 1, the hydraulic pump 73 is located generally adjacent the frame 5 and is connected to the hydraulic cylinder unit 69 by hoses 85 for the flow of high pressure hydraulic fluid to and from the cylinder 75. A solenoid valve (not shown) is connected to one of the hoses 85 to provide on/off control of the hydraulic fluid to the cylinder 75. A switch 89 mounted on the frame 5 is used to actuate the solenoid valve that controls the operation of the cylinder unit 69. In the illustrated embodiment the pump 73 is driven by a 7.5 hp electric motor 93 mounted on the pump and is controlled via an on/off switch 95 located on a wall-mounted control panel 99. A suitable hydraulic pump 73 is a variable displacement hydraulic pump manufactured by Bosch Rexroth Corporation of Hoffman Estates, Ill., Model No. AA10VSO, Series 31, sized for a nominal pressure of 4000 psi (276 bar) and a peak pressure of 5100 psi (352 bar). In the illustrated embodiment, the pump 73 incorporates a sensing circuit including an adjustable pressure regulator 103 mounted on the pump that maintains a constant pressure throughout the hydraulic system so that the pump supplies only the amount of hydraulic fluid to the cylinder 75 that is needed to maintain a set pressure which can be easily adjusted at the pump. It will be understood that the hydraulic cylinder unit 69, hydraulic pump 73, and electric motor 93 may be other sizes, makes, and model numbers without departing from the scope of this invention. Further, the force generating device 67 may comprise a gravity driven mechanism that relies on gravity to generate a downward force, although, the hydraulic cylinder unit 69 and pump 73 are preferable as this system provides a constant, precise amount of force.

A sample holder 109 is removably attached to the piston rod 79 of the hydraulic cylinder unit 69 generally above the enclosure 21. As shown in FIGS. 2 and 3, the sample holder 109 has a body comprising a generally cylindric base 113 with a conical end 117 having a hollow cavity 121 at its free end. In the illustrated embodiment, the holder 109 has a removable head 119 at the conical end 117 of the body that is attached to the base 113 by an adhesive 123 (e.g., double-sided tape). The adhesive 123 between the head 119 and the base 113 of the holder 109 thermally isolates the cavity 121 from the base to allow more efficient cooling of the sample. The free end of the holder 109 comprises a sharp annular edge 125 at the outermost end of the holder 109. The hollow cavity 121 receives a sample S to be frozen in the apparatus 1. The sample S may be a biological tissue sample that is suspended in a solution and placed into the cavity 121 by a dropper or other instrument (not shown). Also, the sample S may consist of a small portion of biological tissue sized to fit in the hollow cavity 121 that may be placed in the cavity with tweezers or forceps (not shown). As shown in FIG. 3, when a sample S is loaded into the cavity 121, the sample typically extends beyond the annular edge 125 of the holder 109 so that the volume of sample is slightly larger than the volume of the cavity. The sample holder 109 comprises a material (e.g., stainless steel) that is considerably harder than the block material (e.g., copper) so that the sharp annular edge 125 of the holder 109 penetrates the surface of the block 29 when the holder is pressed against the block by the force generating device 67.

Figure 4:
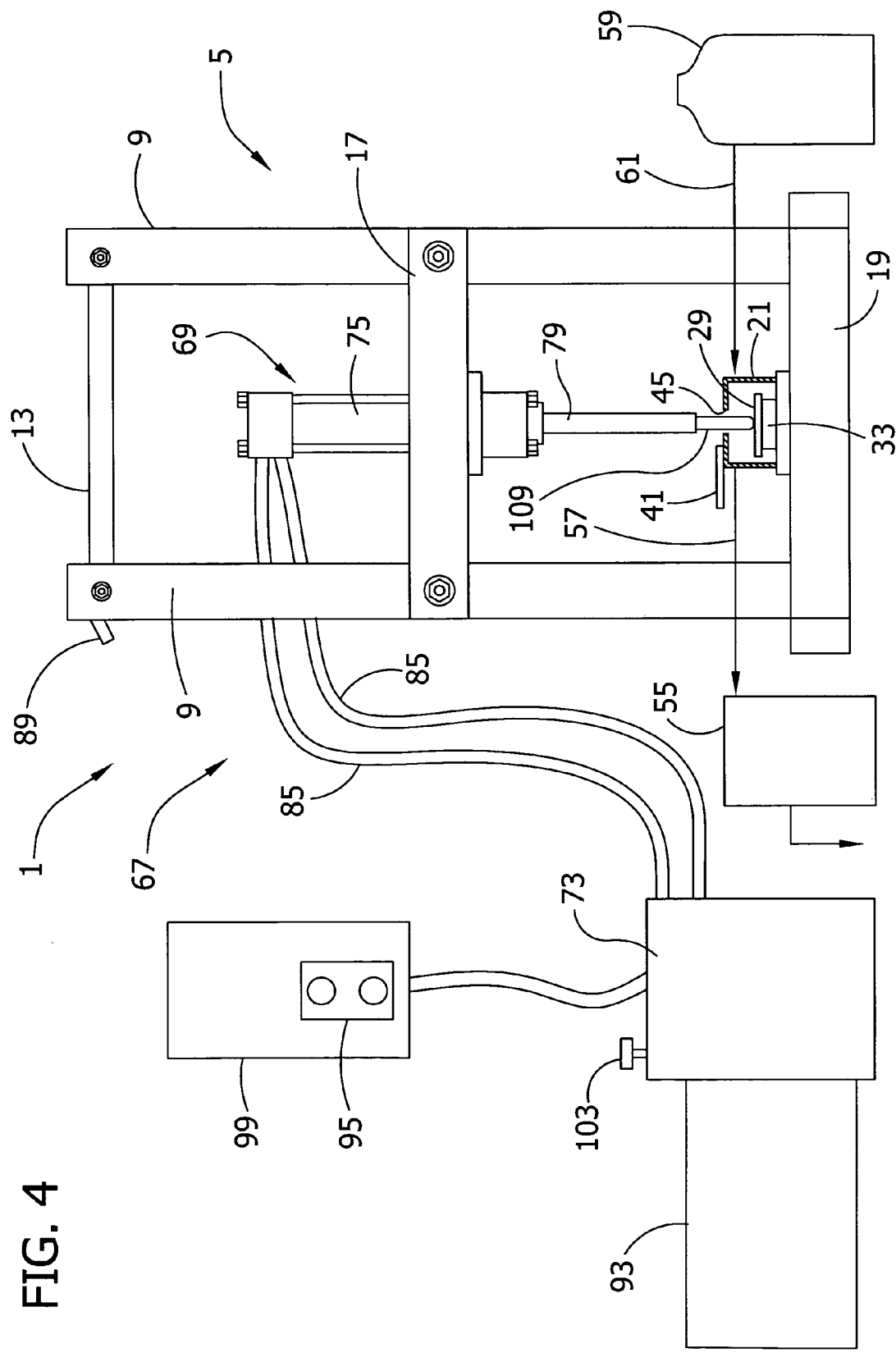
FIG. 4 is an elevation view similar to FIG. 1 but showing the sample holder of the apparatus lowered into a cryogenic chamber of the apparatus.

The sample holder 109 is removably attached to the piston rod 79 of the hydraulic cylinder unit 69 after the sample S has been loaded into the holder. The sample holder 109 may be threadably engaged with the piston rod 79 or may be attached to the piston rod by other means. For example, the base 113 of the sample holder 109 may be received in a hollow end of the piston rod 79 and held in place by a set screw (not shown) or the sample holder may be attached to the piston rod by magnetic attraction. When the piston rod 79 is extended by the cylinder unit 69 (FIG. 4), the sample holder 109 attached to the piston rod is thrust into the cryogenic chamber 25 such that the sample S held in the cavity 121 is pressed against the cold block 29 located in the chamber.

In use, the freezing apparatus 1 of the present invention is operated to freeze the biological sample S by contacting the sample with the block 29 that has been cooled by the flow of cryogenic fluid into the cryogenic chamber 25. The pressing of the sample S against the cold block 29 is commonly referred to as "slamming" or "freeze slamming" the sample. The method of freezing the sample S comprises first lowering the temperature of the block 29 by filling the enclosure 21 with cryogenic fluid by opening the valve from the pressure vessel 59 and operating the vacuum pump 55 to remove air from the enclosure 21. The block 29 should be cooled a sufficient amount of time before loading the sample S into the holder 109 to assure that the block has reached a sufficiently low temperature to effectively freeze the sample. For example, the temperature of the block 29 should be approximately equal to that of the cryogenic fluid in contact with the block and stand 33 prior to loading the sample S into the holder 109. While the block 29 is being cooled, the hydraulic pump 73 is turned on from the wall-mounted control panel 99 to allow adequate pressure in the hydraulic fluid supply lines 85 to build. The hydraulic fluid supplied to the cylinder 69 builds to the predetermined pressure setting of the pressure regulator 103 mounted on the pump 73. The pressure of the hydraulic fluid is monitored by observing a pressure gauge (not shown) mounted on the pressure regulator 103.

After the block 29 has been cooled, the sample S is loaded into the sample holder 109. As stated above, the sample S preferably has a larger volume than the cavity 121 of the holder 109 so that the sample protrudes beyond the annular edge 125 of the holder. The tissue or biological sample S to be frozen may be a tissue sample suspended in a aqueous solution or may be a portion of tissue placed in the cavity 121 of the sample holder 109. After the sample S is prepared and loaded into the sample holder 109, the holder is attached to the piston rod 79 extending downward from the body 75 of the hydraulic cylinder unit 69. As stated above, the sample holder 109 may be attached to the piston rod 79 of the hydraulic cylinder unit 69 by any conventional attachment method (e.g., threaded connection, set screw, magnetic attraction, etc.) without departing from the scope of this invention.

Figure 5:
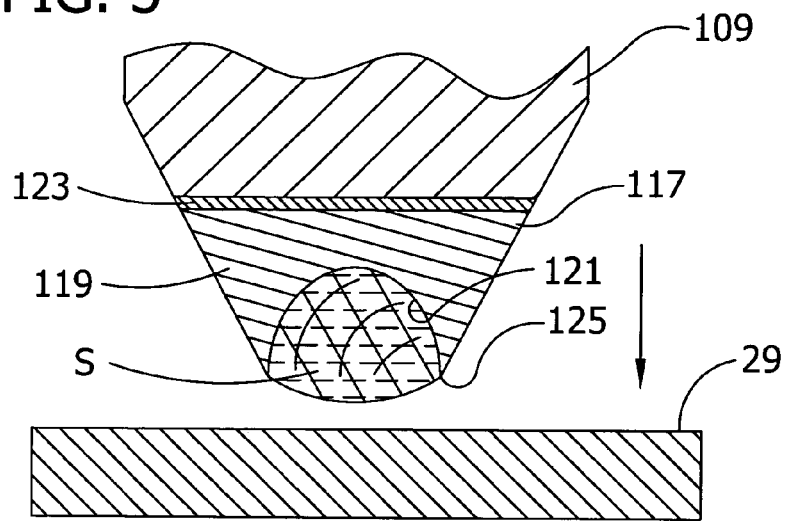
FIG. 5 is an enlarged cross-section of the sample holder prior to contact of the sample with a block of the apparatus.
Figure 6:
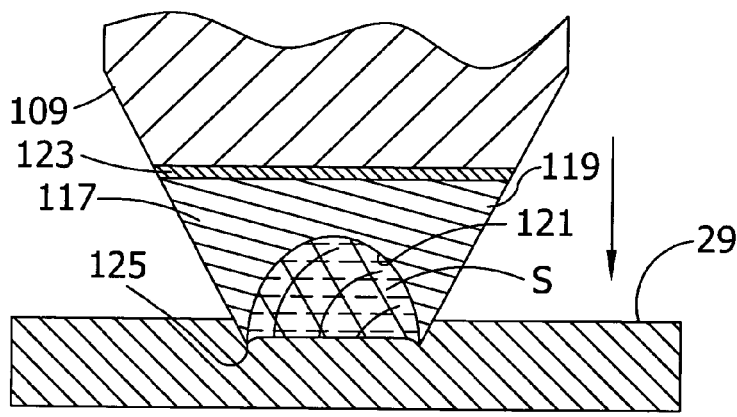
FIG. 6 is an enlarged cross-section similar to FIG. 5 but showing the sample compressed between the holder and the block.
Figure 7:
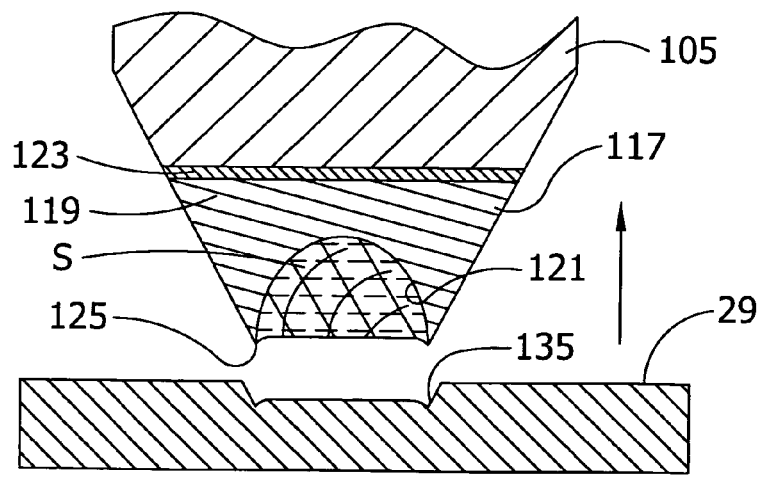
FIG. 7 is an enlarged cross-section similar to FIG. 6 but showing the sample holder removed from the block.

Once the sample holder 109 loaded with sample S has been attached to the piston rod 79, the moveable lid 41 is opened and the force generating device 67 is operated to force the sample and sample holder against the cooled block 29 in the cryogenic chamber 25. The switch 89 mounted on one of the upright members 9 of the frame 5 is positioned to actuate the solenoid valve controlling the flow of hydraulic fluid to the cylinder unit 69. The pressure in the cylinder 75 of the cylinder unit 69 builds and causes the piston rod 79 to extend from the cylinder, pressing the sample holder 109 against the cold block 29. As shown in FIGS. 5-7, the sample holder 109 is pressed against the block 29 with sufficient force that causes the sharp annular edge 125 of the holder to penetrate the top surface of the block. As shown in FIG. 6, the sharp edge 125 of the sample holder 109 as well as a portion of the sample S penetrate the top surface of the block 29 forming a depression 135 on the top surface of the block. When the sample S is pressed against the block 29, it is compressed between the holder 109 and the cold block such that a layer of freezing is formed on the sample. The sample S is pressed against the block 29 with sufficient force such the sample is recessed inward into the cavity 121 from the outer edge of the conical tip 117 of the sample holder 109. The reduction in volume of the sample S is a result of the downward force of the hydraulic cylinder unit 69 that presses the sample holder 109 into the block compressing the sample between the holder and the block 29. The reduction of volume of the sample S is illustrated by comparing the sample before contact with the block 29 (FIG. 5) with the sample after compression between the block and the holder 109 (FIG. 7).

In the illustrated embodiment, the hydraulic cylinder 69 quickly freezes the sample S by pressing the sample against the block 29 by applying a constant downward force that prevents the sample from "bouncing" off the cold block during the freezing process. The sharp annular edge 125 of the sample holder 109 bites into the copper block 29 creating a tight seal between the sharp annular edge and the copper block. The impact of the sample S on the copper block 29 also deforms the copper inside the perimeter of the sharp annular edge 125. However, because the sample S is not as hard as the stainless steel holder 109 the deformation of the copper block 29 inside the perimeter of the annular edge 125 is not as deep. In effect, the copper block 29 protrudes into the cavity 121, significantly reducing its volume. The integrity of the seal of the sharp annular edge 125 of the holder 109 with the copper block 29 prevents the sample S from expanding. Thus, it is not possible for water in the sample S to crystalize as it freezes. Moreover, the depth to which the sample S is frozen is beneficially increased because the entire exposed surface contacts the copper block 29 for the entire time of freezing (i.e., none of the exposed surface bounces off the copper block). The absence of ice crystals greatly improves the quality of the frozen sample S.

The amount of force generated by the hydraulic cylinder 69 may differ based on the specific size of the cylinder and the hydraulic pump 73. Preferably, the cylinder 69 presses the sample holder 109 into the block 29 with enough force to subject the sample S to at least approximately 2000 bar (29,000 psi) of pressure so that the sample is frozen without the formation of ice crystals. Subjecting the sample S to a high compressive force produces a thicker layer of freezing in the sample and reduces the cellular deformation that occurs when water is converted to ice crystals. The length of time that the cylinder unit 69 presses the sample holder 109 into the copper block 29 varies with the size, type, and composition of the sample S being frozen as well as the amount of force being applied to the sample. In one embodiment, the duration of pressure application to the sample S (FIG. 6) is approximately 1-2 seconds.

Because the cross-sectional area of sample holder 109 is smaller than the cross-sectional area of the piston of the cylinder unit 69, the force balance acting on the holder results in a proportionally larger pressure being applied to the sample S than the pressure generated in the cylinder. In one example of the invention, the sample holder 109 attached to the piston rod 79 is sized to have a cavity 121 with a diameter at the tip of the holder of approximately 0.64 $cm_2$ (¼") and a cross-sectional area of approximately 0.32 $cm^2$ (0.05 $in.^2$). The hydraulic pump 73 and cylinder unit 69 provide approximately 344 bar (5,000 psi) pressure acting downward on the piston rod 79 of the cylinder unit which corresponds to a pressure acting on the sample S held in the cavity of approximately 6900 bar (100,000 psi).

In one experiment, a sample S comprising tissue of a frog liver was frozen under the above operating conditions of the apparatus 1 (i.e., subjected to approximately 6900 bar of pressure). After freezing, the sample S was cut into sections at various depths and each section was examined under an electron microscope to determine the approximate depth of the layer of freezing in the sample. Each section of the frozen sample S was examined after being subjected to "freeze substitution", which is a method know in the art of biological sample preparation. In freeze substitution, sub-zero acetone is used to dissolve ice in the frozen sample. If freezing in the sample S was too slow, empty holes or vacancies will be visible where ice crystals were formed in the sample. If no ice crystals exist in the section of sample S, the sample is observed to have a uniform distribution of molecules in every cell. Using freeze substitution and microscopic evaluation of each cross section of the sample S, it was determined that a layer of freezing in the frog liver sample substantially free of ice crystals extended to a depth of approximately 200 μm (8 mil).

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for freezing a biological sample, the apparatus comprising:
   a frame;
   an enclosure adapted to conduct a cryogenic fluid therethrough;
   a block disposed in the enclosure so that the block is cooled to a temperature capable of freezing the sample;
   a force generating device mounted on the frame generally above the enclosure; and
   a sample holder removably attached to the force generating device having a cavity at its free end for receiving a sample to be frozen,
   the force generating device, sample holder, and block being constructed to compress the sample between the block and the sample holder such that the holder penetrates the surface of the block and effectively seals the sample during compression, wherein the block is made of a softer material than the free end of the holder.

2. The apparatus of claim 1 wherein the free end of the sample holder has a sharp edge adapted to penetrate the surface of the block.

3. The apparatus of claim 2 wherein said sharp edge surrounds the cavity of the sample holder.

4. The apparatus of claim 1 wherein said sample holder comprises stainless steel.

5. The apparatus of claim 1 wherein said block comprises copper.

6. The apparatus of claim 1 wherein the force generating device comprises a hydraulic cylinder operatively connected to a hydraulic pump.

7. The apparatus of claim 6 wherein the force generating device further comprises a pressure regulator for maintaining a constant pressure of hydraulic fluid supplied from the pump.

8. The apparatus of claim 1 wherein the hydraulic cylinder is force generating device is adapted to compress the sample between the block and the sample holder to a pressure of at least 2000 bar.

9. The apparatus of claim 8 wherein the force generating device is adapted to compress the sample between the block and the sample holder to a pressure of at least 5000 bar.

10. The apparatus of claim 1 wherein said enclosure comprises a top wall having a lid that is moveable between an open position allowing access to the cryogenic chamber and a closed position to promote efficient cooling of the block.

11. The apparatus of claim 1 further comprising a reservoir for supplying cryogenic fluid into the enclosure to cool the block.

12. The apparatus of claim 11 further comprising a vacuum pump for evacuating the enclosure during cooling of the block.

13. The apparatus of claim 12 wherein said cryogenic fluid is liquid nitrogen.

14. A sample holder for use in a freezing apparatus for freezing a sample for microscopic evaluation by using a force generating device to press the sample against a cold block, the sample holder comprising a body adapted to be attached to the force generating device, the body having a cavity at its free end adapted to receive a sample to be frozen, the free end of the body having an edge margin adapted to sealingly engage the block of the freezing apparatus so that the sample held in the cavity is compressed between the block and the body of the sample holder, the edge margin of the holder being adapted to penetrate a surface of the cold block, wherein the edge margin of the body comprises a sharp edge adapted to penetrate the surface of the block so that the sample held in the cavity is compressed between the body of the holder and the block.

15. The sample holder of claim 14 wherein the sharp edge of the holder is an annular edge around the sample-receiving cavity.

16. The sample holder of claim 14 wherein said body comprises a generally cylindric base, a conical tip housing the sample-receiving cavity, and a thermal baffler between the conical tip and the base.

17. The sample holder of claim 16 wherein the conical tip is removably attached to the base.

18. The sample holder of claim 17 wherein the thermal barrier comprises an adhesive removably attaching the conical tip to the base.

19. The sample holder of claim 14 wherein the body is made of stainless steel.

20. A method of freezing a sample for microscopic evaluation comprising:
    lowering the temperature of a metal block to a temperature capable of freezing the sample;
    loading a sample into a sample holder made of a harder material than the block;
    attaching the sample holder to a force generating device; and
    operating the force generating device so that the sample is cooled by contact with the block and the sample holder penetrates and deforms a surface of the block thereby sealing the cavity and compressing the sample between the sample holder and the block.

21. The method of claim 20 wherein loading a sample comprises placing a biological tissue sample in a cavity of the sample holder.

22. The method of claim 21 wherein lowering the temperature comprises at least partially filling an enclosure around the block with cryogenic fluid.

23. The method of claim 22 wherein operating the force generating device comprises receiving material of the block into the cavity for compressing the biological tissue sample.

24. The method of claim 22 wherein lowering the temperature comprises operating a vacuum pump to create a vacuum in the enclosure.

25. The method of claim 22 wherein the force generating device comprises a hydraulic cylinder in fluid communication with a hydraulic pump and attaching the sample holder comprises connecting the sample holder to the hydraulic cylinder.

26. The method of claim 25 wherein operating the force generating device comprises turning on the hydraulic pump causing extension of the hydraulic cylinder to force the sample against the block.

27. The method of claim 25 wherein operating the force generating device comprises monitoring the fluid pressure supplied by the pump to maintain a constant compression force acting on the sample.

28. The method of claim 20 wherein operating the force generating device comprises compressing the sample between the block and the sample holder to a pressure of at least 2000 bar.

29. The method of claim 28 wherein operating the force generating device comprises compressing the sample between the block and the sample holder to a pressure of at least 5000 bar.

* * * * *

UNITED STATES PATENT AND TRADEMARK OFFICE
CERTIFICATE OF CORRECTION

PATENT NO. : 7,293,426 B2 Page 1 of 1
APPLICATION NO. : 10/962810
DATED : November 13, 2007
INVENTOR(S) : John E. Heuser It is certified that error appears in the above-identified patent and that said Letters Patent is hereby corrected as shown below:

Column 1, Line 3-5 after the title and before "BACKGROUND OF THE INVENTION," please add the following paragraph:

-- STATEMENT OF GOVERNMENT RIGHTS
This invention was made with Government support under grant number GM029647 awarded by the National Institutes of Health. The Government has certain rights in the invention. --

Signed and Sealed this

Sixteenth Day of February, 2010

David J. Kappos
*Director of the United States Patent and Trademark Office*